US008481783B2

(12) United States Patent
Simon

(10) Patent No.: US 8,481,783 B2
(45) Date of Patent: Jul. 9, 2013

(54) PROCESS OF SEPARATION OF GLYOXYLIC ACID FROM AN AQUEOUS REACTION MEDIUM CONTAINING GLYOXYLIC ACID AND HYDROCHLORIC ACID

(75) Inventor: Olivier Simon, Jaux (FR)

(73) Assignee: Clariant Speciality Fine Chemicals (France), Nanterre (FR)

( * ) Notice: Subject to any disclaimer, the term of this patent is extended or adjusted under 35 U.S.C. 154(b) by 339 days.

(21) Appl. No.: 12/864,412

(22) PCT Filed: Jan. 21, 2009

(86) PCT No.: PCT/EP2009/050663
§ 371 (c)(1),
(2), (4) Date: Aug. 24, 2010

(87) PCT Pub. No.: WO2009/092736
PCT Pub. Date: Jul. 30, 2009

(65) Prior Publication Data
US 2010/0312011 A1 Dec. 9, 2010

(30) Foreign Application Priority Data
Jan. 25, 2008 (FR) ...................... 08 50469

(51) Int. Cl.
*C07C 51/44* (2006.01)
*C07C 59/153* (2006.01)
(52) U.S. Cl.
USPC ........... 562/577; 562/539; 562/540; 562/538; 562/580
(58) Field of Classification Search
None
See application file for complete search history.

(56) References Cited

U.S. PATENT DOCUMENTS

| 3,779,876 | A | * | 12/1973 | Michelet | ................... 205/443 |
|---|---|---|---|---|---|
| 4,146,731 | A | | 3/1979 | Ogahara et al. | |
| 4,698,441 | A | | 10/1987 | Mitani et al. | |
| 5,091,566 | A | | 2/1992 | Schouteeten et al. | |
| 5,138,096 | A | | 8/1992 | Schouteeten et al. | |
| 2011/0012056 | A1 | | 1/2011 | Bleger et al. | |

FOREIGN PATENT DOCUMENTS

| CN | 1634847 | 7/2005 |
|---|---|---|
| EP | 0349406 | 1/1990 |
| EP | 0428429 | 5/1991 |
| FR | 2372141 | 6/1978 |
| FR | 2516506 | 5/1983 |
| JP | 58153575 | 12/1983 |

OTHER PUBLICATIONS

English Translation of CN 1634874, Dec. 2, 2004.
International Search Report for PCT/EP2009/050661, dated Jul. 9, 2009.
Translation of Written Opinion of the Internatonal Searching Authority for PCT/EP2009/050661, dated Apr. 8, 2010.
International Search Report for PCT/EP2009/050663, dated Apr. 14, 2009.
Written Opinion of the International Searching Authority for PCT/EP2009/050663, dated Apr. 14, 2009.
English Abstract for JP 58 153575, Mar. 4, 1982.
Chemical Engineering and Processing, 33, (1994), 247-260.
Zhou Zhi-ming, et al., "A Novel Synthesis of Glyoxylic Acid with $O_2$ Catalysed by Nitrogen Oxide", Transactions of Beijing Institute of Technology, vol. 25, No. 5, May 2005.

* cited by examiner

*Primary Examiner* — Yevegeny Valenrod
(74) *Attorney, Agent, or Firm* — Tod A. Waldrop

(57) ABSTRACT

The invention relates to a process for separating glyoxylic acid starting from an aqueous reaction medium containing glyoxylic acid and hydrochloric acid, comprising a step of countercurrent steam stripping of the reaction medium in order to obtain, on the one hand, a gas phase containing the volatile hydrochloric acid and, on the other hand, a liquid phase containing the purified glyoxylic acid.

18 Claims, 1 Drawing Sheet

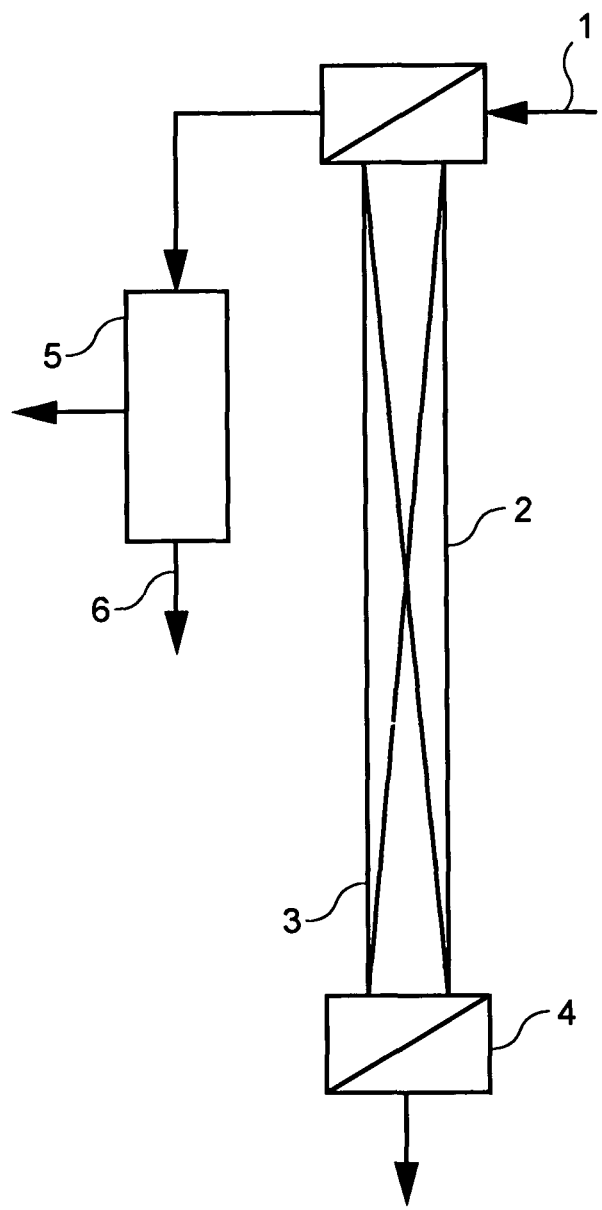

PROCESS OF SEPARATION OF GLYOXYLIC ACID FROM AN AQUEOUS REACTION MEDIUM CONTAINING GLYOXYLIC ACID AND HYDROCHLORIC ACID

The invention relates to a process for purifying glyoxylic acid starting from an aqueous reaction medium containing glyoxylic acid and hydrochloric acid, which makes it possible to significantly reduce the residual concentration of hydrochloric acid in the medium.

Glyoxylic acid is usually obtained by oxidation of glyoxal using nitric acid in the presence of an inorganic acid such as hydrochloric acid, in an aqueous medium, as described, for example, in application EP 349 406.

The general principle of this oxidation is the following:

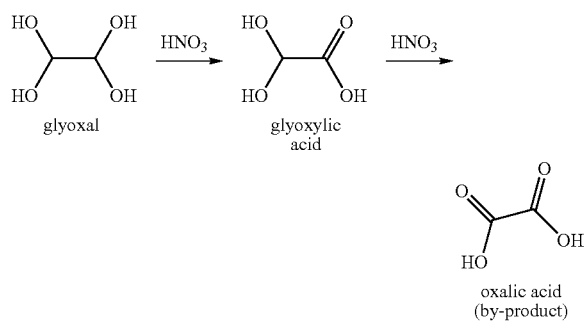

The aqueous solutions of glyoxylic acid obtained contain a not insignificant amount of hydrochloric acid that it is difficult to eliminate.

Techniques such as evaporation, electrodialysis or treatment with ion exchange resins are customarily used.

However, these techniques are not satisfactory from the industrial point of view because they require a large input of energy, in particular in the case of electrodialysis, or else the use of large amounts of resins. Furthermore, the usual evaporation techniques, which result in the formation of an azeotropic hydrochloric acid-water mixture, do not make it possible to reduce the hydrochloric acid content below that of the azeotropic mixture.

Application JP 58-153575 describes a process for purifying an aqueous solution of glyoxylic acid using operating conditions which make it possible to avoid the formation of an azeotropic hydrochloric acid-water mixture. A ternary glyoxylic acid-hydrochloric acid-water mixture is formed, and the hydrochloric acid is extracted from this mixture. It is indicated that this process is preferably applied to aqueous solutions of glyoxylic acid comprising less than 60% by weight of glyoxylic acid.

However, none of these techniques manages to reduce the hydrochloric acid content below a content of the order of 5000 ppm, although such a content poses problems of corrosion on most materials for constructing equipment or storage materials, and it is desired to reduce it to approximately 300 ppm or less.

Furthermore, it has been noted that, the higher the glyoxylic acid content in an aqueous medium, for example through concentration, the more difficult it becomes to reduce the hydrochloric acid content, in particular due to the viscosity of the concentrated glyoxylic acid.

The technical problem to be solved therefore consists in providing a process for purifying glyoxylic acid starting from an aqueous reaction medium containing glyoxylic acid and hydrochloric acid, which makes it possible to significantly reduce the residual concentration of hydrochloric acid in the medium, and which can be implemented on the industrial level without the need for a large consumption of energy or of reactants.

According to a first aspect, the invention therefore relates to a process for separating glyoxylic acid starting from an aqueous reaction medium containing glyoxylic acid and hydrochloric acid, comprising a step of countercurrent steam stripping of the reaction medium in order to obtain, on the one hand, a gas phase containing the volatile hydrochloric acid and, on the other hand, a liquid phase containing the purified glyoxylic acid.

Advantageously, the process according to the invention is carried out in an aqueous reaction medium containing less than 30% by weight of water, preferably less than 25% by weight of water.

The countercurrent stripping step is carried out under a pressure less than atmospheric pressure, preferably less than 30000 Pa (300 mbar), and more particularly less than 10000 Pa (100 mbar).

The aqueous reaction medium containing glyoxylic acid and hydrochloric acid is advantageously obtained by oxidation of glyoxal in the presence of hydrochloric acid.

The process according to the invention may be advantageously implemented when the hydrochloric acid concentration in the aqueous reaction medium is less than or equal to 2% by weight, in particular less than or equal to 0.5% by weight.

As indicated above, the process according to the invention is particularly suitable for reducing the residual content of hydrochloric acid in the aqueous reaction medium to very low contents.

In particular, the process according to the invention makes it possible to reduce the hydrochloric acid concentration in the liquid phase containing the purified glyoxylic acid to a content of less than or equal to 250 ppm, preferably less than or equal to 100 ppm, preferentially less than or equal to 50 ppm, and more preferentially less than or equal to 30 ppm.

As indicated above, the process according to the invention is particularly suitable for the purification of aqueous reaction media containing a high concentration of glyoxylic acid.

In particular, the process according to the invention may be implemented when said aqueous reaction medium contains 70% to 80% by weight of glyoxylic acid, 0 to 5% by weight of oxalic acid and 0 to 5% by weight of glyoxal.

According to one preferred aspect of the process according to the invention, a steam to reaction medium ratio of between 0.1 and 10 by weight, in particular between 0.2 and 2 by weight, is used.

A device for implementing the process according to the invention is represented schematically in FIG. 1.

Any steam stripping device can be used in the present invention, such as packed columns (loose packing or ordered packing) or tray columns.

At (1), the aqueous reaction medium containing glyoxylic acid and hydrochloric acid is introduced at the top of a glass column (2) with thermal insulation comprising Raschig rings, in which the countercurrent steam introduced at (3) at the bottom of the column circulates. The liquid phase containing the purified glyoxylic acid solution is recovered at the bottom of the column by means of a gas-liquid separator (4). At the top of the column, the gas phase is condensed in a heat exchanger (5) and recovered at (6).

According to another preferred aspect of the invention, the aqueous reaction medium containing glyoxylic acid and hydrochloric acid is preheated before being introduced into the column, preferably at a temperature of between 50 and 100° C., and most particularly between 60 and 90° C.

The invention is illustrated in a nonlimiting manner by the examples below.

EXAMPLE 1

1) Preparation of an Aqueous Reaction Mixture Containing Glyoxylic Acid and Hydrochloric Acid A commercially available aqueous solution of glyoxylic acid at 50% by weight (Clariant Specialty Fine Chemicals (France)) is concentrated to 77% and then aqueous hydrochloric acid at 37% is added so as to obtain an aqueous solution of glyoxylic acid at 76% by weight containing approximately 5000 ppm of hydrochloric acid.

2) Separation of the Glyoxylic Acid

The aqueous solution of glyoxylic acid obtained above, preheated to 80° C., is introduced with a flow rate of 3894 g/h above a glass column (50 mm in diameter, 2 m in length) which is thermally insulated and filled with Rashig rings (6×6 mm). The steam is introduced at the bottom of the column with an introduction flow rate of 2001 g/l. The pressure in the column is less than 10000 Pa (100 mbar). An aqueous solution of glyoxylic acid at 75% by weight, containing 32 ppm of hydrochloric acid, is recovered at the bottom of the column with a flow rate of 3944 g/l.

EXAMPLE 2

Example 1 is reproduced, but using an aqueous solution of glyoxylic acid at 80% by weight containing approximately 5000 ppm by weight of hydrochloric acid with an introduction flow rate of 2363 g/h and a steam flow rate of 1599 g/h.

An aqueous solution of glyoxylic acid at 74% by weight, containing 39 ppm of hydrochloric acid, is recovered at the bottom of the column with a flow rate of 2581 g/l.

The invention claimed is:

1. A process for separating glyoxylic acid starting from an aqueous reaction medium containing glyoxylic acid and hydrochloric acid, comprising a step of countercurrent steam stripping of the reaction medium to obtain, a gas phase containing the volatile hydrochloric acid and a liquid phase containing the purified glyoxylic acid.

2. A process according to claim 1, wherein the aqueous reaction medium contains less than 30% by weight of water.

3. A process according to claim 1, wherein the aqueous reaction medium contains less than 25% by weight of water.

4. A process according to claim 1, wherein the countercurrent stripping step is carried out under a pressure less than atmospheric pressure.

5. A process according to claim 4, wherein the countercurrent stripping step is carried out under a pressure of less than 30000 Pa.

6. A process according to claim 1, wherein the aqueous reaction medium containing glyoxylic acid and hydrochloric acid is obtained by oxidation of glyoxal in the presence of hydrochloric acid.

7. A process according to claim 1, wherein the hydrochloric acid concentration in the aqueous reaction medium is less than or equal to 2% by weight.

8. A process according to claim 1, wherein the hydrochloric acid concentration in the aqueous reaction medium is less than or equal to 0.5% by weight.

9. A process according to claim 1, wherein the hydrochloric acid concentration in the liquid phase containing the purified glyoxylic acid is less than or equal to 250 ppm.

10. A process according to claim 9, wherein the hydrochloric acid concentration in the liquid phase containing the purified glyoxylic acid is less than or equal to 50 ppm.

11. A process according to claim 1, wherein the aqueous reaction medium contains 70% to 80% by weight of glyoxylic acid, 0 to 5% by weight of oxalic acid and 0 to 5% by weight of glyoxal.

12. A process according to claim 1, wherein the steam to reaction medium ratio is between 0.1 and 10 by weight.

13. A process according to claim 12, wherein the steam to reaction medium ratio is between 0.2 and 2 by weight.

14. A process according to claim 1, wherein the aqueous reaction medium containing glyoxylic acid and hydrochloric acid is preheated.

15. A process according to claim 1, wherein the aqueous reaction medium containing glyoxylic acid and hydrochloric acid is preheated to a temperature between 50 and 100° C.

16. A process according to claim 9, wherein the hydrochloric acid concentration in the liquid phase containing the purified glyoxylic acid is less than or equal to 30 ppm.

17. A process according to claim 4, wherein the countercurrent stripping step is carried out under a pressure of less than 10000 Pa.

18. A process according to claim 1, wherein the hydrochloric acid concentration in the liquid phase containing the purified glyoxylic acid is less than or equal to 100 ppm.

* * * * *